United States Patent
Nygard et al.

(10) Patent No.: US 10,357,658 B2
(45) Date of Patent: Jul. 23, 2019

(54) IMPLANTABLE AUDITORY PROSTHESIS USAGE RESTRICTION

(71) Applicant: Cochlear Limited, Macquarie University, NSW (AU)

(72) Inventors: Tony Mikael Nygard, Terrigal (AU); Jan Raymond Janssen, St. Ives (AU)

(73) Assignee: COCHLEAR LIMITED, Macquarie University (AU)

( * ) Notice: Subject to any disclaimer, the term of this patent is extended or adjusted under 35 U.S.C. 154(b) by 97 days.

(21) Appl. No.: 15/600,839

(22) Filed: May 22, 2017

(65) Prior Publication Data
US 2018/0333577 A1 Nov. 22, 2018

(51) Int. Cl.
*A61N 1/00* (2006.01)
*A61N 1/372* (2006.01)
*H04R 25/00* (2006.01)
*A61N 1/36* (2006.01)
(Continued)

(52) U.S. Cl.
CPC ....... *A61N 1/37247* (2013.01); *A61N 1/0541* (2013.01); *A61N 1/36036* (2017.08); *A61N 1/36038* (2017.08); *A61N 1/36039* (2017.08); *A61N 1/3787* (2013.01); *A61N 1/37258* (2013.01); *H04R 25/70* (2013.01); *H04R 25/60* (2013.01); *H04R 25/606* (2013.01); *H04R 2225/67* (2013.01)

(58) Field of Classification Search
CPC ............ A61N 1/36032; A61N 1/37247; A61N 1/0541; A61N 1/36036; A61N 1/36038; A61N 1/36039; A61N 1/37258; A61N 1/3787; H04R 25/60; H04R 2225/67; H04R 25/606; H04R 25/70
See application file for complete search history.

(56) References Cited

U.S. PATENT DOCUMENTS

2006/0025833 A1* 2/2006 Daly .................. A61N 1/36036
607/55
2009/0240307 A1 9/2009 Seligman
2013/0070946 A1 3/2013 Kroman
(Continued)

FOREIGN PATENT DOCUMENTS

KR 101496237 B1 3/2015

OTHER PUBLICATIONS

International Search Report and Written Opinion in corresponding International Application No. PCT/IB2018/053389, dated Oct. 23, 2018.

*Primary Examiner* — George Manuel
(74) *Attorney, Agent, or Firm* — Edell, Shapiro & Finnan, LLC

(57) ABSTRACT

An implantable auditory prosthesis includes at least one implantable sound sensor that is configured to detect sound signals from within a recipient and to use these internally detected sound signals for use in stimulating the recipient. The implantable auditory prosthesis is also configured to receive sound signals from an external sound source and to use the externally detected sound signals for use in stimulating the recipient. The implantable auditory prosthesis uses the sound signals received from the external sound source to stimulate the recipient, while restricting the use of sound signals detected at the implantable sound sensor when the external sound source is not present/available to provide sound signals to the implantable auditory prosthesis.

20 Claims, 6 Drawing Sheets

(51) Int. Cl.
*A61N 1/378* (2006.01)
*A61N 1/05* (2006.01)

(56) References Cited

U.S. PATENT DOCUMENTS

2014/0275730 A1 9/2014 Lievens et al.
2016/0199644 A1 7/2016 Van den Heuvel

* cited by examiner

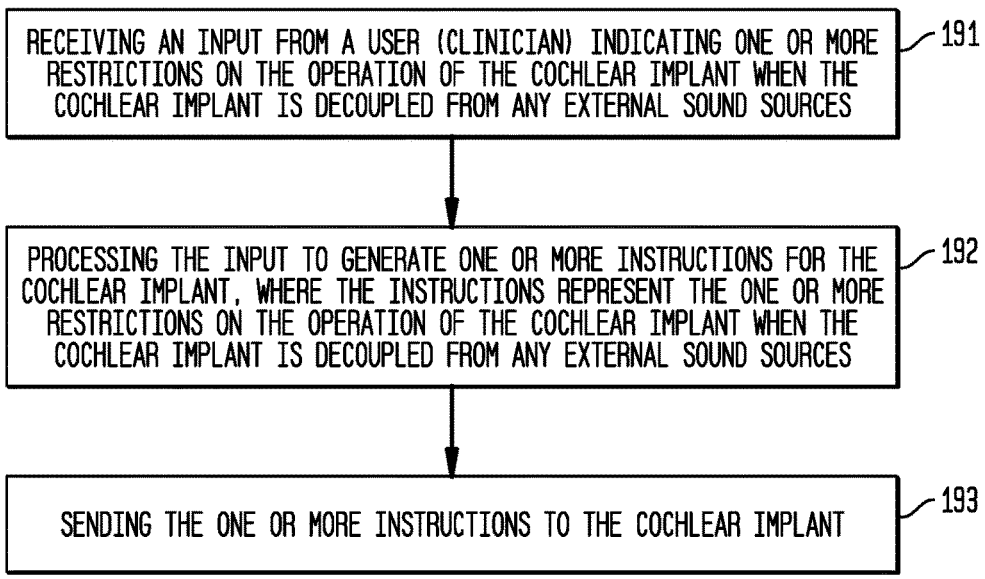

IMPLANTABLE AUDITORY PROSTHESIS USAGE RESTRICTION

BACKGROUND

Field of the Invention

The present invention relates generally to implantable auditory prostheses.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

SUMMARY

In one aspect, a totally implantable component of a hearing prosthesis system is provided. The totally implantable component comprises: an implantable microphone; an implantable battery; a stimulator unit configured to stimulate a recipient of the totally implantable component to evoke a hearing percept when the totally implantable component is in communication with an external component of the hearing prosthesis system; and a controller configured to limit stimulation of the recipient, irrespective of the charge level in the implantable battery, when the totally implantable component is not in communication with the external component.

In another aspect, a fitting system is provided. The fitting system comprises: a device interface for communication with an implantable auditory prosthesis implanted in a recipient, wherein the implantable auditory prosthesis comprises an implantable microphone and a stimulator unit; a user interface configured to receive an input from a user restricting operation of the implantable auditory prosthesis when the implantable auditory prosthesis is not in communication with any external sound sources; and one or more processors configured to process the input to generate one or more instructions, where the instructions represent the one or more restrictions on the operation of the implantable auditory prosthesis when the implantable auditory prosthesis is not in communication with any external sound sources, and to send the one or more instructions to the implantable auditory prosthesis for instantiation thereof.

In another aspect, an implantable auditory prosthesis implantable in a recipient is provided. The implantable auditory prosthesis comprises: at least one implantable sound sensor configured to detect internal sound signals from within the recipient; a stimulator unit operable to generate stimulation signals for delivery to a recipient of the auditory prosthesis; and a controller configured to restrict usage of the internal sound signals in the generation of stimulation signals for delivery to the recipient when the implantable auditory prosthesis is unable to communicate with at least one external sound source.

BRIEF DESCRIPTION OF THE DRAWINGS

Embodiments of the present invention are described herein in conjunction with the accompanying drawings, in which:

FIG. 3 is a flowchart of a method, in accordance with certain embodiments presented herein;

DETAILED DESCRIPTION

Certain auditory prostheses are referred to as being "totally implantable," meaning that all components are implanted in a recipient and the prostheses are able to operate, for at least a finite period of time, without any external devices. These totally implantable prostheses generally include one or more internal/implantable sound sensors that are used to detect/receive sound signals from within the recipient. These auditory prostheses are also configured to process the sound signals detected from within the recipient and to generate stimulation signals for delivery to the recipient to evoke perception of the sound signals.

Merely for ease of illustration, the techniques presented herein are primarily described with reference to one type of implantable auditory prosthesis, namely a totally implantable cochlear implant. However, it is to be appreciated that the techniques presented herein may be used in other implantable auditory prostheses, such as totally implantable acoustic implants, auditory brainstem stimulators, etc.

Figure 1A:
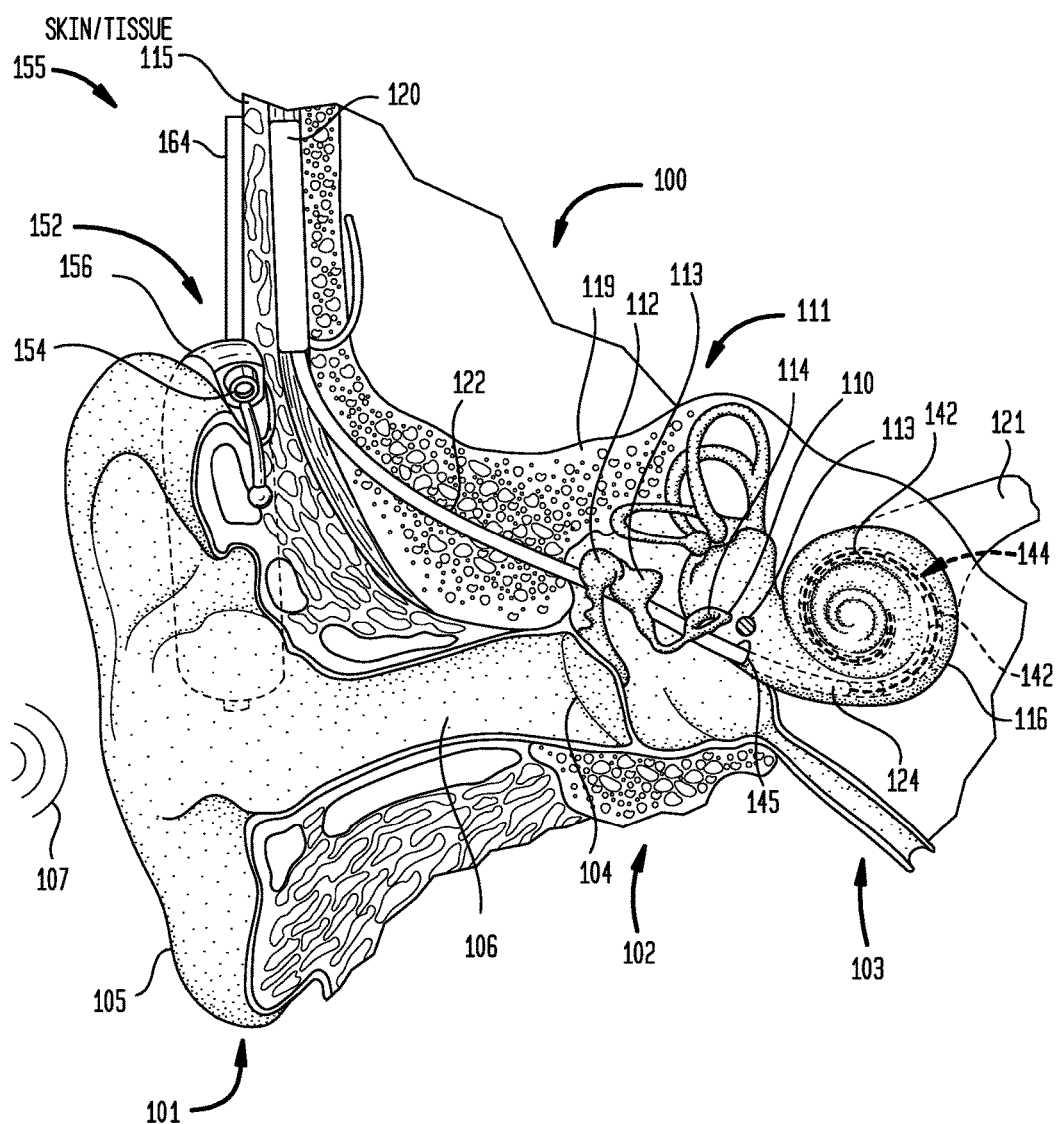
FIG. 1A is a schematic diagram illustrating a totally implantable cochlear implant, in accordance with certain embodiments presented herein.
Figure 1B:
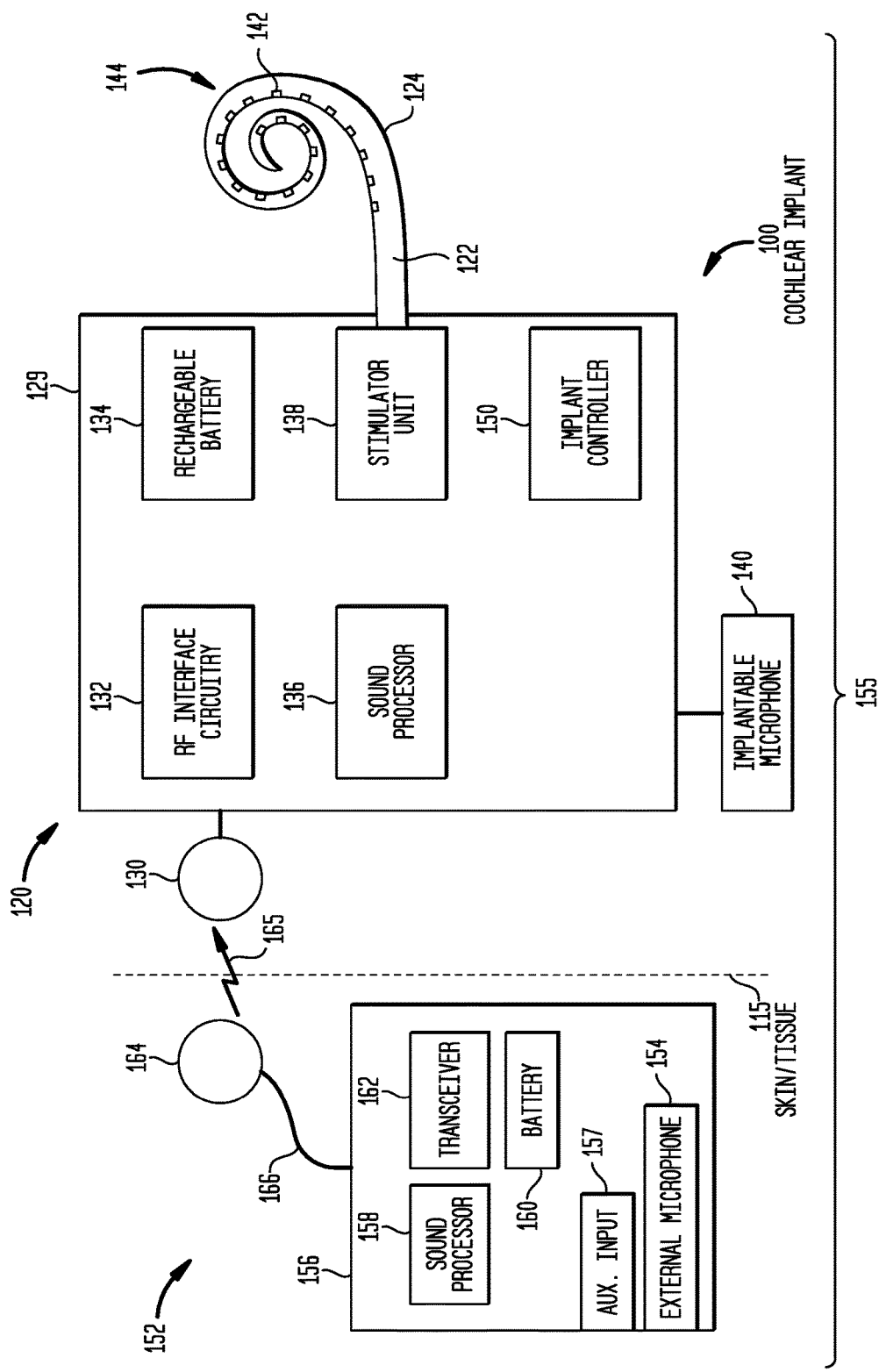
FIG. 1B is a block diagram of the totally implantable cochlear implant of FIG. 1A.

FIG. 1A is schematic diagram of an exemplary totally cochlear implant 100 configured to implement embodiments of the present invention, while FIG. 1B is a block diagram of the totally implantable cochlear implant 100. For ease of description, FIGS. 1A and 1B will be described together. The cochlear implant 100 is referred to as being a "totally implantable" cochlear implant because all components of the cochlear implant are configured to be implanted under skin/tissue 115 of a recipient. Because all components of totally implant cochlear implant 100 are implantable, the cochlear implant operates, for at least a finite period of time, without the need of an external device.

Shown in FIG. 1A is an outer ear 101, a middle ear 102 and an inner ear 103 of the recipient. In a fully functional human hearing anatomy, the outer ear 101 comprises an auricle 105 and an ear canal 106. Sound signals 107, sometimes referred to herein as acoustic sounds or sound waves, are collected by the auricle 105 and channeled into and through the ear canal 106. Disposed across the distal end of the ear canal 106 is a tympanic membrane 104 which vibrates in response to the sound signals (i.e., sound waves) 107. This vibration is coupled to the oval window or fenestra ovalis 110 through three bones of the middle ear 102, collectively referred to as the ossicular chain or ossicles 111 and comprising the malleus 112, the incus 113 and the stapes 114. The ossicles 111 of the middle ear 102 serve to filter and amplify the sound signals 107, causing oval window 110 to vibrate. Such vibration sets up waves of fluid motion within the cochlea 116 which, in turn, activates hair cells (not shown) that line the inside of the cochlea 116. Activation of these hair cells causes appropriate nerve impulses to be transferred through the spiral ganglion cells and the auditory nerve 118 to the brain (not shown), where they are perceived as sound.

As noted above, sensorineural hearing loss may be due to the absence or destruction of the cochlea hair cells, which transduce acoustic signals into nerve impulses. One treatment for such sensorineural hearing loss is a cochlear implant, such as totally implantable cochlear implant 100 shown in FIGS. 1A and 1B, which bypasses the cochlear hair cells and delivers stimulation (e.g., electrical stimulation) directly to the cochlea nerve cells.

In the embodiments of FIGS. 1A and 1B, the cochlear implant 100 comprises an implant body (main module) 120, a lead region 122, and an elongate intra-cochlear stimulating assembly 124. The implant body 120 comprises a hermetically sealed housing 129 in which radio frequency (RF) interface circuitry 132 (sometimes referred to as a transceiver unit), at least one rechargeable battery 134, a sound processor 136, a stimulator unit 138, and at least one implant controller/processor 150 are disposed. The implant body 120 also comprises an internal/implantable coil 130, generally disposed outside of the housing 129, and at least one implantable sound sensor/transducer 140 (e.g., implantable microphone), which may be located within the housing 129 or external to the housing 129. As such, although for ease of illustration the implantable sound sensor 140 is shown within housing 129, it is to be appreciated that cochlear implant 100 can include implantable sound sensors that have other implanted positions/locations.

The RF interface circuitry 132 is connected to the implantable coil 130 and a magnet (not shown) is fixed relative to the implantable coil 130. Implantable coil 130 is typically a wire antenna coil comprised of multiple turns of electrically insulated single-strand or multi-strand platinum or gold wire. The electrical insulation of implantable coil 130 is provided by a flexible molding (e.g., silicone molding), which has been omitted from FIG. 1B. The implantable coil 130 and the RF interface circuitry 132 enable the transfer of power and/or data from an external device to the cochlear implant 100. However, it is to be appreciated that various types of energy transfer, such as infrared (IR), electromagnetic, capacitive and inductive transfer, may be used to transfer power and/or data from an external device to a cochlear implant 100 and, as such, FIG. 1B illustrates only one example arrangement.

Elongate stimulating assembly 124 is configured to be at least partially implanted in cochlea 116 and includes a plurality of longitudinally spaced intra-cochlear electrical stimulating contacts (electrical contacts) 142 that collectively form a contact array 144. Stimulating assembly 124 extends through an opening in the cochlea 116 (e.g., cochleostomy 145, oval window 110, the round window 113, etc.) and has a proximal end connected to stimulator unit 138 via lead region 122 that extends through mastoid bone 119. Lead region 122 couples the stimulating assembly 124 to implant body 120 and, more particularly, to stimulator unit 138.

As noted above, the cochlear implant 100 comprises at least one implantable sound sensor 140 that is configured to detect sound signals and to convert the detected sound signals into electrical signals. These electrical signals are received by the sound processor 136, which is configured to execute sound processing and coding to convert the electrical signals into processed signals that represent the detected sound signals. The processed signals are then provided to the stimulator unit 138, which is configured to utilize the processed signals to generate electrical stimulation signals that are delivered to the recipient's cochlea via one or more electrodes 142 implanted in the recipient's cochlea 116. In this way, cochlear implant 100 stimulates the recipient's auditory nerve cells, bypassing absent or defective hair cells that normally transduce acoustic vibrations into neural activity.

As detailed above, the cochlear implant 100 is a totally implantable device that is configured to: (1) detect/receive sound signals from within the recipient, (2) process the sound signals, and (3) generate stimulation signals for delivery to the recipient to evoke perception of the sound signals. Also as noted above, the sound signals are detected via one or more implantable sound sensors (e.g., implantable microphone 140). When compared with signals detected at external sound sensors, the internally detected sound signals can have a lower signal quality. As a result, the use of implantable sound sensors for some types of recipients, and/or some types of hearing environments, may in some circumstances be undesirable and, potentially, unacceptable.

To address these concerns, the cochlear implant 100 is configured to: (1) operate with an external device that is configured to detect sound signals (i.e., an external sound source), and (2) to restrict/limit the use of sound signals detected by implantable microphone 140 in stimulating the recipient. That is, the external sound source provides sound signals to the cochlear implant 100, and the cochlear implant is configured to use those signals from the external sound source to stimulate the recipient. However, when the external device is not present/available to provide sound signals to the recipient, the cochlear implant 100 restricts/limits the use of sound signals detected at the implantable microphone 140.

For example, the totally implantable cochlear implant 100 is configured to operate with at least one external sound source 152. The totally implantable cochlear implant 100 and the external sound source 152 are sometimes collectively referred to herein as a cochlear implant system 155. For ease of illustration, FIGS. 1A and 1B illustrate the external sound source 152 in the form of a behind-the-ear (BTE) sound processing unit. However, it is to be appreciated that totally implantable cochlear implants in accordance with embodiments presented herein may be used with any of a variety of devices that are configured to provide sound signals, including BTE units, off-the-ear headpiece units (i.e., button processor units), in-the-ear (ITE) devices, wireless microphones, etc. As such, an external sound source in accordance with embodiments presented herein may be any external device that is configured to provide sound signals to an implantable auditory prosthesis, such as a totally implantable cochlear implant. It is also to be appreciated that, as used herein, the term "sound signals" refers to acoustic sounds that have been converted into electrical signals, either in a processed or unprocessed form. In addition, the term "external sound signals" is used herein to refer to any sound signals that are provided to cochlear implant 100 from an external sound source, such as BTE sound processing unit 152. The term "internal sound signals" is used herein to refer to any sound signals that are detected/received at the implantable sound sensor(s) (e.g., implantable microphone 140) of the cochlear implant 100.

The BTE sound processing unit 152 in FIGS. 1A and 1B includes a housing 156 that is configured to be worn on the outer ear 105 of the recipient. The BTE sound processing unit 152 also comprises one or more external sources which, in the examples of FIGS. 1A and 1B, comprise an external microphone 154 and an auxiliary input (e.g., telecoil, audio input port, etc.) 157. Although FIG. 1B illustrates the external microphone within housing 156, it is to be appreciated that the external microphone 154 may also or alternatively be located outside of the housing.

The BTE sound processing unit 152 further comprises a sound processor 158, a power source 160 (e.g., a battery), and a transceiver unit (transceiver) 162. The external sound sources (e.g., external microphone 154 and/or the auxiliary input 157) are configured to detect/receive sound signals. In this example, the sound processor 158 is configured to process electrical signals generated by the external sound sensors and to generate processed sound signals therefrom.

The transceiver 162 is electrically connected to the external coil 164 via, for example, a cable 166. The external coil 164 is typically a wire antenna coil comprised of multiple turns of electrically insulated single-strand or multi-strand platinum or gold wire and is configured to be inductively coupled to the implantable coil 130. As such, the transceiver 162 is configured to use the external coil 164 to send the processed sound signals generated by the sound processor 136 to the cochlear implant 100. In FIG. 1B, the processed sound signals sent from the BTE sound processing unit 152 to the cochlear implant 100 are schematically illustrated by arrow 165.

When the BTE sound processing unit 152 is able to provide external sound signals to the cochlear implant 100, the cochlear implant is configured so as to operate (by default) in an "external hearing mode." In the external hearing mode, the cochlear implant 100 uses the processed sound signals 165 (e.g., the external sound signals) received from the BTE sound processing unit 152 to stimulate the recipient. The cochlear implant 100 can use the processed sound signals 165 alone or in combination with and internal sound signals detected by the implantable microphone 140. For example, in one illustrative arrangement, the stimulator unit 138 is configured to receive both the processed sound signals 165 (generated by the BTE sound processing unit 152) as well as processed sound signals generated by the sound processor 136 (i.e., internal sound signals) and the stimulator unit 138 is configured to suppress any internal sound signals detected at the implantable microphone 140 (e.g., the implant controller 150 configures the stimulator unit 138 so as to use only the processed sound signals 165 generated by the BTE sound processing unit 152 to generate stimulation signals for delivery to the recipient). In another arrangement, the sound processor 136 may receive both the processed sound signals 165 as well as internal sound signals from the implantable microphone 140 and can be configured (e.g., by the implant controller 150) to either suppress any internal sound signals or mix the internal sound signals with the processed sound signals 165. It is to be appreciated that these examples are illustrative and that the cochlear implant 100 could operate in a number of different manners so as to use external sound signals to stimulate the recipient.

An external sound source, such as BTE sound processing unit 152, is able to provide sound signals to the cochlear implant 100 when the BTE sound processing unit is in communication with the cochlear implant 100. This condition may be evaluated/determined by the cochlear implant 100. In certain examples, the cochlear implant 100 may also evaluate/determine whether the BTE sound processing unit 152 is operational to provide external sound signals (e.g., powered on, fully operational, etc.). For example, in the embodiment of FIGS. 1A and 1B, the cochlear implant 100 is configured to determine when the BTE sound processing unit 152, and more specifically the external coil 164, is inductively coupled to the implantable coil 130 (thereby indicating that the BTE sound processing unit 152 is in communication with the cochlear implant 100). Using the inductive coupling, the cochlear implant 100 can use a number of techniques to determine whether or not the BTE sound processing unit 152 is powered on and/or functioning properly (thereby indicating that the BTE sound processing unit 152 is operational to provide external sound signals).

As noted, the cochlear implant 100 operates in the external hearing mode (i.e., uses the processed sound signals 165) when the cochlear implant 100 is in communication with the BTE sound processing unit 152 and/or operational to provide external sound signals. In accordance with embodiments presented herein, the cochlear implant 100 is configured to operate in a "restricted hearing mode" when the cochlear implant 100 is not in communication with BTE sound processing unit 152 (or another external sound source) and/or the BTE sound processing unit 152 is otherwise unable to provide external sound signals to the cochlear implant. That is, when the cochlear implant 100 determines that the BTE sound processing unit 152 is unable to provide external sound signals, the implant controller 150 is configured restrict/limit operations of the cochlear implant 100.

The restricted hearing mode of an implantable auditory prosthesis, such as cochlear implant 100, may take a number of different forms that can be selected based on a number of different factors. For example, in certain embodiments, when the cochlear implant 100 enters the restricted hearing mode, the implant controller 150 is configured to substantially immediately restrict/limit (e.g., disable/prevent, dampen, etc.) the delivery of stimulation to the recipient, irrespective of the charge level in the implantable battery 134. That is, in these embodiments the implant controller 150 configures one or more of the sound processor 136 or the stimulator unit 138 so as to limit the generation of stimulation signals based on any internal sound signals detected at the implantable microphone 140. In one alternative embodiment, when the cochlear implant 100 enters the restricted hearing mode, the implant controller 150 is configured to substantially immediately limit operation of the cochlear implant (e.g., power down the cochlear implant). In each of these embodiments, the implant controller 150 could initiate the generation of at least one of an external audible or visual alert to a caretaker or other user indicating that the cochlear implant 100 is no longer delivering stimulation signals to the recipient.

Collectively, the above two embodiments illustrate techniques for limiting the use of internal sound signals for generation of stimulation for delivery to the recipient. These restrictions are counter-intuitive given that the cochlear implant 100 already includes an implantable microphone 140 that enables the cochlear implant to operate without any external devices (i.e., to operable invisibly). However, as detailed elsewhere herein, these express restrictions added by the embodiments presented herein provide a deliberately added mechanism to promote good hearing and/or developmental outcomes by limiting the use of "invisible hearing".

The restricted hearing mode of a cochlear implant in accordance with embodiments presented herein is configured to generally limit the use of internal sound signals for generation of stimulation for delivery to the recipient. However, further embodiments may enable additional operations when, for example, the cochlear implant first enters the restricted mode, periodically while in the restricted hearing mode, etc.

For example, in one embodiment, when the cochlear implant 100 first enters the restricted hearing mode (e.g., when the implant controller 150 determines that the implantable coil 130 is decoupled from the external coil 164 and/or determines that the BTE sound processing unit 152 is otherwise unable to provide external sound signals), the implant controller 150 enables the cochlear implant 100 to stimulate the recipient using internal sound signals for a only selected/limited period of time. That is, for a configurable/selected limited period of time after determining that the BTE sound processing unit 152 is unable to provide external sound signals, the implant controller 150 enables the sound processor 136 to process signals generated by the implantable microphone 140 and enables the stimulator unit 138 to use the signals output by the sound processor 136 to generate stimulation signals for delivery to the recipient. In some situations, the switch to invisible hearing may not be immediately apparent to the recipient (e.g. when the sound processor is deactivated because the battery is depleted). The cochlear implant 100 can convey the altered operating mode (i.e. the switch to restricted hearing) to the recipient using an audible notification (e.g. a sudden reduction in perceived volume). At the end of the limited period of time, the implant controller 150 configures one or more of the sound processor 136 or the stimulator unit 138 so as to limit the further generation of stimulation signals based on internal sound signals detected at the implantable microphone 140. In certain embodiments, once the time limit has been reached, the implant controller 150 could initiate the generation of at least one of an external audible or visual alert for the recipient, a caretaker or other user indicating that the cochlear implant 100 is no longer delivering stimulation signals to the recipient or is delivering repressed stimulation signals (such as significantly damped signals that provide environmental awareness but limited sound discrimination).

In certain embodiments, while the cochlear implant 100 operates in the restricted hearing mode, the sound processor 136 is configured to process the internal sound signals detected at the implantable microphone 140 and the implant controller 150 selectively enables the delivery of stimulation to the recipient based on one or more attributes of the internal sound signals (e.g., when one or more attributes of the internal sound signals satisfy predetermined criteria). The one or more attributes of the internal sound signals may include, for example, content of the internal sound signals (e.g., a level/loudness of the sound signals), a sound/acoustic environment in which the recipient is located, etc.

For example, in one such embodiment, the implant controller 150 is configured to determine when the internal sound signals include loud sounds, such as warnings, alerts, etc. When the loudness (level) of the internal sound signals exceeds a certain threshold, the implant controller 150 can selectively allow the stimulator unit 138 to use the signals output by the sound processor 136 to generate stimulation signals for delivery to the recipient. As a result, these embodiments expand the restricted hearing mode so that the recipient is able to perceive loud sounds, but is still unable to rely on the implantable microphone 140 as the primary sound capture mechanism.

In another embodiment, the implant controller 150 is configured to evaluate/analyze the internal sound signals to determine the sound class of the sound signals and selectively enable the delivery of stimulation to the recipient based thereon. That is, the implant controller 150 can be configured to use the internal sound signals to "classify" the ambient sound environment in which the recipient is located into one or more sound categories (i.e., determine the input signal type or classify the sound signals)). The sound classes/categories may include, but are not limited to, "Speech," "Noise," "Speech+Noise," "Music," and "Quiet." Based on the determined sound class/category, the implant controller 150 can selectively allow the stimulator unit 138 and the sound processor 136 to use the internal sound signals detected at the implantable microphone 140 to generate stimulation signals for delivery to the recipient. As a result, these embodiments expand the restricted hearing mode so that the recipient is able to perceive sounds in, for example, low noise environments (e.g., a "Quiet" environment), but is still unable to rely on the implantable microphone 140 as the primary sound capture mechanism.

In a further embodiment, rather than determining the sound class of the internal sound signals, the implant controller 150 could directly analyze/evaluate a noise level (e.g., signal-to-noise ratio (SNR)) associated with the internal sound signals and selectively enable the delivery of stimulation to the recipient based thereon. That is, the implant controller 150 can be configured to determine whether a noise level of the internal sound signals is greater than (or alternatively less than) a selected noise threshold. If the noise level is sufficiently low (e.g., below the noise threshold), then the implant controller 150 can selectively allow the stimulator unit 138 to use the signals output by the sound processor 136 to generate high fidelity stimulation signals for delivery to the recipient (i.e. simulation signals that allow sufficient sound discrimination for e.g. speech perception). In situations where the recipient is exposed to unacceptable noise levels for a sustained period, the cochlear implant 100 can repress the stimulation signals generated from the implanted sensor (such as significantly damping the signals that provide environmental awareness but limited sound discrimination). As a result, these embodiments expand the restricted hearing mode so that the recipient is able to perceive internal sound signals that only include relatively low noise levels.

In certain embodiments, while the cochlear implant 100 operates in the restricted hearing mode (e.g., when the implant controller 150 determines that the implantable coil 130 is decoupled from the external coil 164 and/or determines that the BTE sound processing unit 152 is otherwise unable to provide external sound signals), the implant controller 150 may be configured to selectively enable the delivery of stimulation to the recipient during certain time periods each day. That is, the implant controller 150 can be configured to determine a current a time-of-day (ToD) and to selectively allow the stimulator unit 138 and the sound processor 136 to use the internal sound signals detected at the implantable microphone 140 to generate stimulation signals for delivery to the recipient only during certain times of the day (e.g., at night when the recipient is likely sleeping). As a result, these embodiments expand the restricted hearing mode during certain times each day.

Although the above embodiment selectively allow the stimulator unit 138 to use the internal sound signals detected at the implantable microphone 140 based on a ToD, in other embodiments, these operations can be triggered by other mechanisms. For example, the implant controller 150 could be configured to detect/determine the presence of an external charging device (e.g., pillow charger) and, when a selected external charging device is present, selectively allow the sound processor 136 and the stimulator unit 138 to use the internal sound signals detected at the implantable microphone 140 to generate stimulation signals for delivery to the recipient.

Any of the above or other embodiments of the restricted hearing mode may be implemented alone, in various combinations, or may include other extensions/restrictions. In addition, the implant controller 152 may be generally configured to cause the cochlear implant 100 to initiate the generation of at least one of an audible or visual alert when the controller has performed various actions.

It is also to be appreciated that the specific operations that are enabled in the restricted hearing mode may depend on a number of different factors and may be different for individual recipients. As such, the operations of the implant controller 150 and other components of the cochlear implant 100 during the restricted hearing mode, as well as when the cochlear implant 100 enters the restricted hearing mode, can be set/programmed by a clinician/audiologist based on the needs of a user. That is, the restricted hearing mode of an implantable auditory prosthesis, such as cochlear implant 100, can be configured/programmed by a clinician during, for example, a fitting session.

Figure 2:
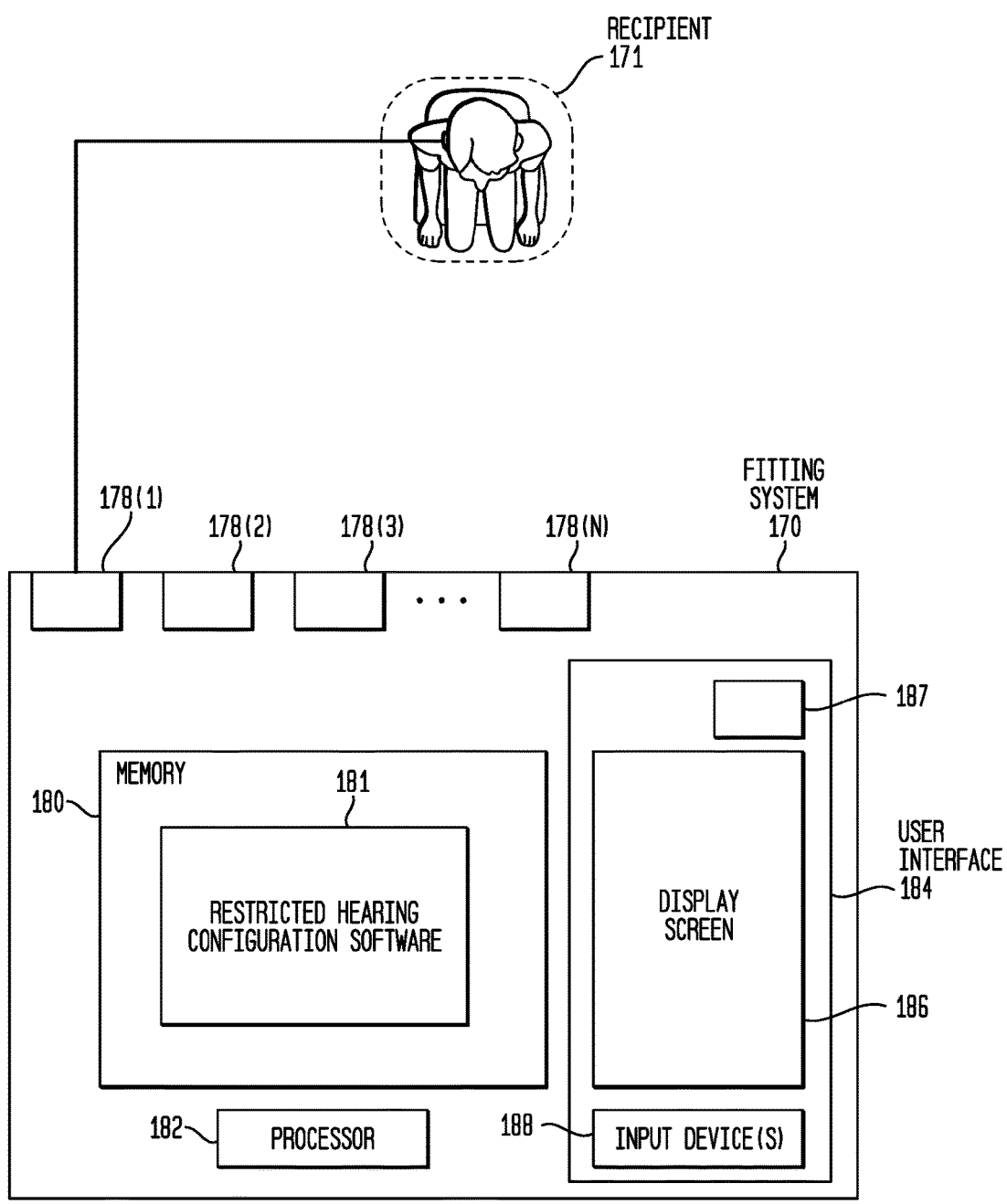
FIG. 2 is a block diagram of a fitting system, in accordance with certain embodiments presented herein.

FIG. 2 is a schematic diagram illustrating a fitting system 170 in accordance with embodiments presented herein that can be used to program/configure a restricted hearing mode of an implantable auditory prosthesis. For ease of illustration, fitting system 170 is described with reference to totally implantable cochlear implant 100 of FIGS. 1A and 1B.

Fitting system 170 is, in general, a computing device that comprises a plurality of interfaces/ports 178(1)-178(N), a memory 180, a processor 182, and a user interface 184. Stored in memory 180 is restricted hearing configuration software (logic) 181. The interfaces 178(1)-178(N) may comprise, for example, any combination of network ports (e.g., Ethernet ports), wireless network interfaces, Universal Serial Bus (USB) ports, Institute of Electrical and Electronics Engineers (IEEE) 1194 interfaces, PS/2 ports, etc. Interface 178(1) may be directly connected to the cochlear implant 100 or connected to a device (e.g., remote control device, behind-the-ear processing unit, etc.) that is communication with the cochlear implant 100. Interfaces 178(1)-178(N) may be configured to transmit/receive signals via a wired or wireless connection (e.g., telemetry, Bluetooth®, etc.). Bluetooth is a registered trademark of Bluetooth SIG, Inc.

The user interface 184 includes one or more output devices, such as a liquid crystal display (LCD) screen 186 and/a speaker 187, for presentation of visual or audible information to a clinician, audiologist, or other user. The user interface 184 may also comprise one or more input devices 188 that include, for example, a keypad, keyboard, mouse, touchscreen, etc.

Memory 180 may comprise read only memory (ROM), random access memory (RAM), magnetic disk storage media devices, optical storage media devices, flash memory devices, electrical, optical, or other physical/tangible memory storage devices. The processor 182 is, for example, a microprocessor or microcontroller that executes instructions for the restricted hearing configuration software 181. Thus, in general, the memory 180 may comprise one or more tangible (non-transitory) computer readable storage media (e.g., a memory device) encoded with software comprising computer executable instructions and when the software is executed (by the processor 182) it is operable to enable a clinician to configure/set restricted hearing operations of the cochlear implant 100.

More specifically, in accordance with the embodiments presented herein, the restricted hearing configuration software 181 enables a clinician to use the user interface 184 to configure/set how the cochlear implant 100 operates when in the restricted hearing mode. In general, the restricted hearing configuration software 181 provides a variety of options for the clinician to program the limited use of invisible hearing in the restricted hearing mode versus use of the external hearing modes (e.g., the limited usage time period, the acceptable sound environments, sound levels, noise levels, or other sound attribute levels or thresholds), instructions for logging and monitoring usage related to all of the above, etc.). That is, the restricted hearing configuration software 181 may enable the clinician to set if/how the implant controller 150 is to selectively enable the delivery of stimulation to the recipient, such as during certain time periods, in response to different sounds, based on different sound attributes, etc. The restricted hearing configuration software 181 may also enable a clinician to use the user interface 184 to configure/set how the cochlear implant 100 enters or exits the restricted hearing mode (i.e., how the restricted hearing mode is to be detected and triggered by the implant controller 150). The restricted hearing configuration software 181 may be configured to generate and expose any of a number of fitting functions, as needed or as requested by the clinician. In one example embodiment, the display screen 186 is configured to display a plurality of selectable options for restricting operation of the cochlear implant 100 when the cochlear implant is unable to communicate with any external sound sources and a clinician may select one of the displayed options for implementation by the restricted hearing configuration software 181.

In general, the restricted hearing configuration software 181 operates as an element in a more general cochlear implant fitting/programming software so as to enable a clinician to control the use of internal sound signals and, as such, limit the ability for the recipient to hear sounds without the presence of an external sound source (i.e., limit the recipient's ability to achieve "invisible" hearing). As noted above, such limitations on the ability to use "invisible" hearing are counter-intuitive to current cochlear implant operation, but are useful for certain recipients where the use of internal sound signals (i.e., sounds detected at implantable sound sensors) could be detrimental to good developmental outcomes. It is envisaged that, as the hearing development of a particular recipient improves, the use of the restricted hearing mode may be reduced or eliminated entirely such that the recipient can primarily rely on his/her implantable sound sensors without the need for external devices (i.e., eventually operate primarily in the invisible hearing mode). Therefore, in accordance with embodiments presented herein, the restricted hearing configuration software 181 can enable a clinician to re-configure or eliminate the restricted hearing operations of the cochlear implant 100 at subsequent times (e.g., after an initial fitting session).

FIG. 3 is a flowchart of a fitting method 190 that may be performed at the fitting system 170 of FIG. 2. Fitting method 190 begins at 191 where, at user interface 184, the fitting system 170 receives an input from a user (clinician) indicating one or more restrictions on the operation of the cochlear implant 100 when the cochlear implant 100 is decoupled from any external sound sources. At 192, the fitting system 170 (e.g., processor 182 executing restricted hearing configuration software 181) processes the input and generates one or more instructions for the cochlear implant 100 based on the input. In general, the instructions represent the one or more restrictions on the operation of the cochlear implant 100 when the cochlear implant 100 is decoupled from any external sound sources. At 193, the fitting system 170 sends the one or more instructions to the cochlear implant 100, where the instructions are instantiated for subsequent use. In one example of FIG. 3, the user interface 184 receives an input indicating a limitation on the ability of the cochlear implant 100 to use sound signals detected by the implantable microphone 140 for stimulating the recipient when the cochlear implant 100 is decoupled from any external sound sources.

Figure 4A:
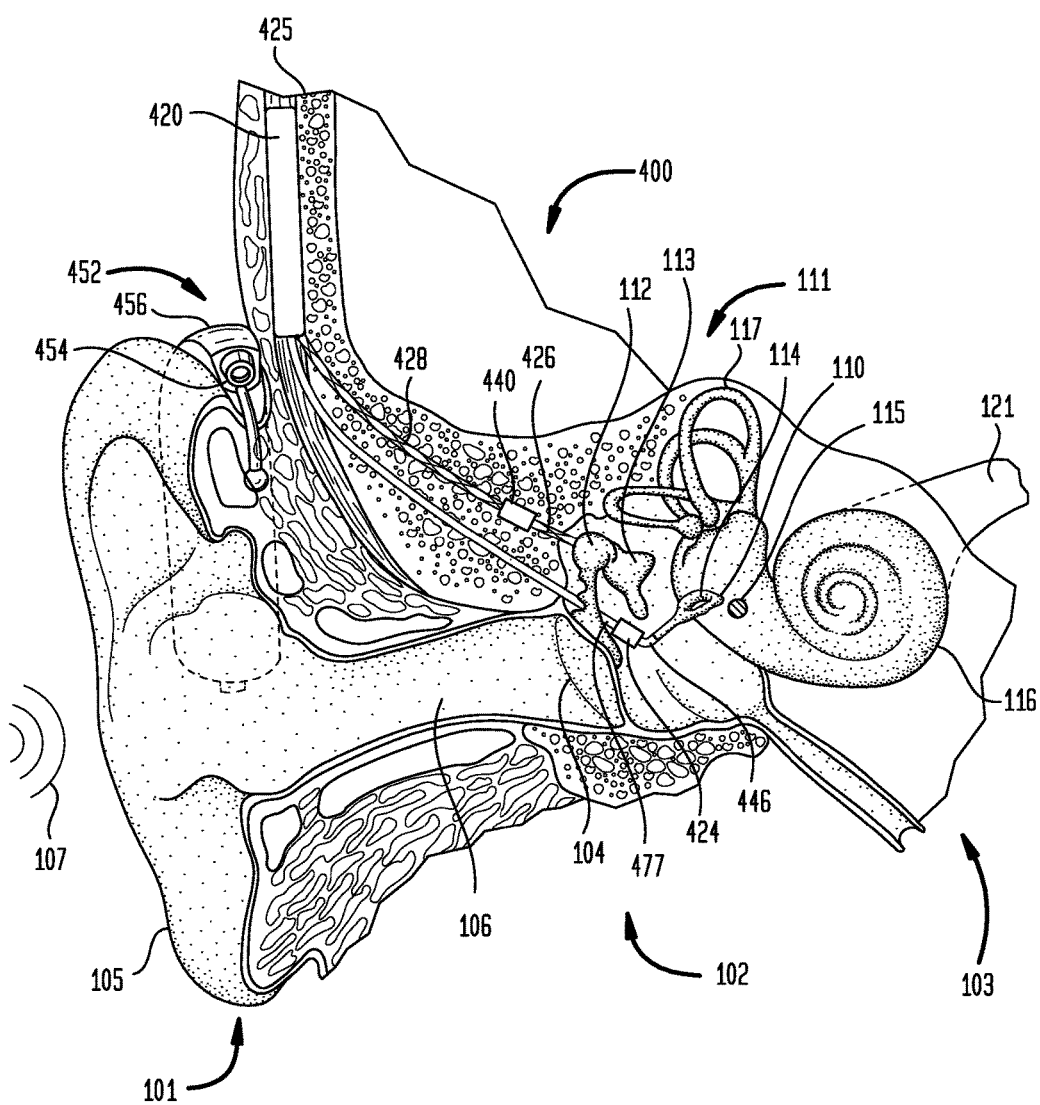
FIG. 4A is a schematic diagram illustrating a totally implantable acoustic implant, in accordance with certain embodiments presented herein.
Figure 4B:
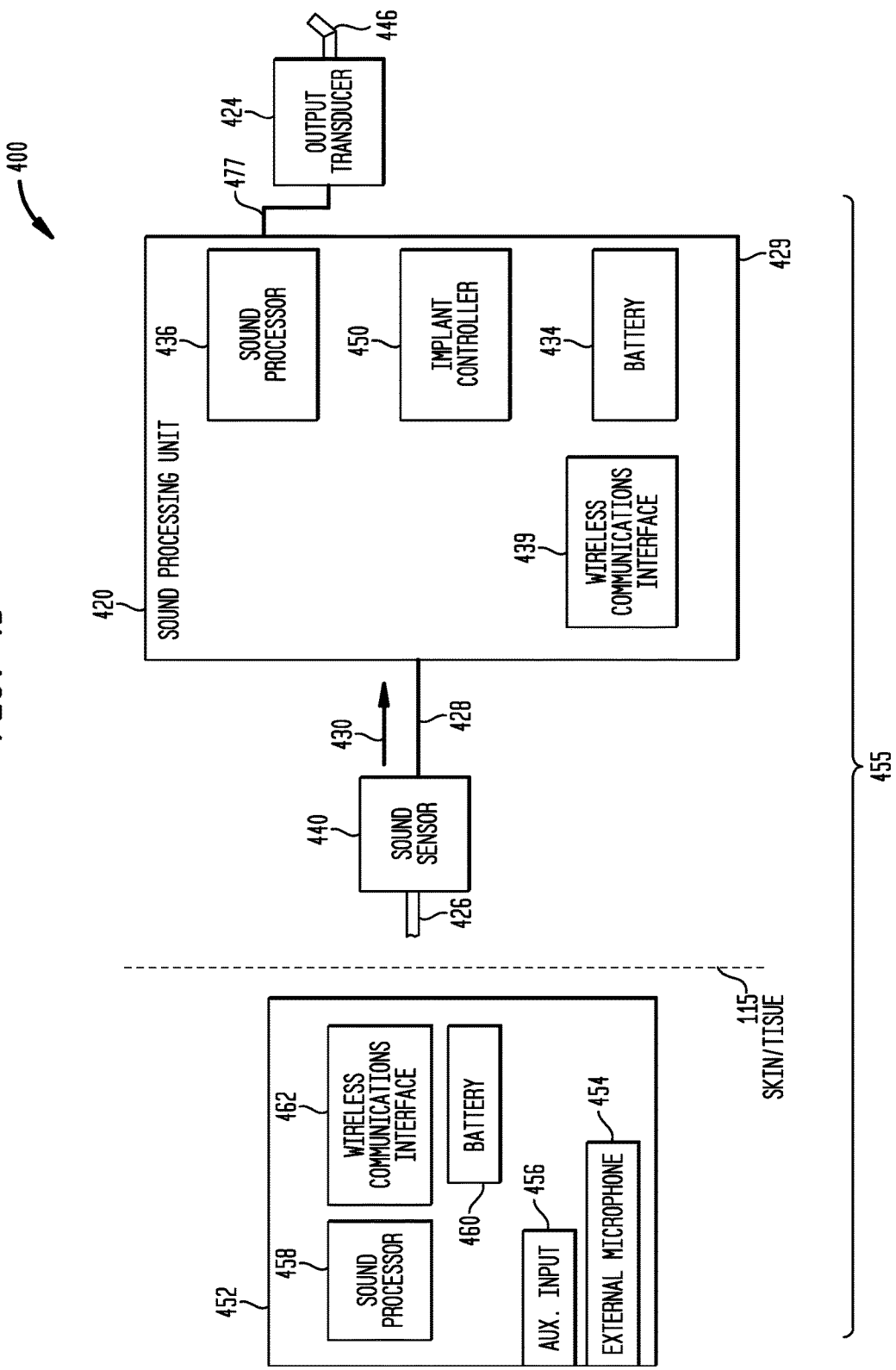
FIG. 4B is a block diagram of the totally implantable acoustic implant of FIG. 4A.

Embodiments of the present invention have been primarily described above with reference to a totally implantable cochlear implant. However, as noted, the techniques presented herein are not limited to implementation in cochlear implants, but instead may be implemented in a number of different types of implantable auditory prostheses. For example, FIG. 4A is a schematic diagram illustrating totally implantable acoustic implant 400 in accordance with embodiments presented herein. The totally implantable acoustic implant 400 is shown implanted in the head 425 of a recipient. FIG. 4B is a block diagram of the totally implantable acoustic implant 400. For ease of description, FIGS. 4A and 4B will be described together.

Shown in FIG. 4A is the outer ear 101, middle ear 102 and an inner ear 103 of the recipient 425. In a recipient with conductive hearing loss, the hearing loss may be due to an impediment to the normal mechanical pathways that provide sound to the hair cells in the cochlea 116. One treatment for conductive hearing loss is the use of an implantable acoustic implant, such implantable acoustic implant 400, that is configured to convert sound signals entering the recipient's outer ear 101 into mechanical vibrations that are directly or indirectly transferred to the cochlea 116, thereby causing generation of nerve impulses that result in the perception of the received sound.

The totally implantable acoustic implant 400 comprises an implanted sound sensor (microphone) 440, a sound processing unit 420, and an output transducer (stimulator unit) 424. The sound sensor 440, sound processing unit 420, and the output transducer 424 are all implanted in the head 425 of the recipient. The sound sensor 440 and the output transducer 424 may each include hermetically-sealed housings which, for ease of illustration, have been omitted from FIGS. 4A and 4B.

The sound sensor 440 is mechanically coupled to an auditory element of the recipient's ear that vibrates in response to receipt of sound signals 107, such as the tympanic membrane 104, the ossicles 111 (e.g., one or more of the malleus 112, the incus 113 or the stapes 114), the oval window 110, the recipient's round window 113, semicircular canals 117, etc. In the illustrative embodiment of FIGS. 1A and 1B, the sound sensor 440 is mechanically coupled to the malleus 112 via a coupling element 426.

In the embodiment of FIGS. 4A and 4B, the outer ear 101 is functional and, as noted above, is able to collect and channel sound signals 107 through the ear canal 106. The sound signals 107 cause the tympanic membrane 104 to vibrate which, in turn, causes vibration of the malleus 112. As noted, the sound sensor 440 is mechanical coupled to the malleus 112 via a coupling element 426 that relays the vibration of the malleus 112 to the sound sensor. The sound sensor 440 is configured to convert the vibration of the malleus 112 (detected by virtue of the mechanical coupling to the malleus 112) into electrical signals that are provided to the sound processing unit 420 via a lead (e.g., one or more hermetically sealed wires) 428. FIG. 4B schematically illustrates electrical signals 430 that are generated by the sound sensor 440 based on (in response to) vibration of the malleus 112 and, accordingly, in response to receipt of the sound signals 107. In the embodiment of FIGS. 4A and 4B, the stapes 114 is disarticulated (dissected) from the malleus 112 and the incus 113.

In certain embodiments, the sound sensor 440 is a piezo-electric (piezo) sensor. A piezoelectric sensor is a type of sound sensor that includes a piezoelectric material that senses vibrations (e.g., vibrations of the malleus 112 via a coupling element 426). The piezoelectric material generates electrical signals that correspond to the sensed vibration. In general, piezoelectric sensors are passive components that do not require power to operate. In other embodiments, the sound sensor 440 can be a subcutaneous microphone, a tube microphone, an electro-magnetic microphone, etc.

As shown in FIG. 4B, the sound processing unit 420 comprises a sound processor 436, at least one rechargeable battery 434, a wireless communications interface 439, and an implant controller 450, all of which are disposed in a hermetically-sealed housing 429. In general, the wireless communications interface 439 comprises one or more elements that enable the totally implantable acoustic implant to wirelessly communicate with one or more external devices, such as an external sound source. The at least one rechargeable battery 434 is configured to supply power to the other components of the totally implantable acoustic implant 400. For ease of illustration, connections between the at least one rechargeable battery 434 and the various powered components of the totally implantable acoustic implant 400 have been omitted from FIG. 4B.

As noted above, the totally implantable acoustic implant 400 comprises at least one implantable sound sensor 440 that is configured to detect sound signals and to convert the detected sound signals into electrical signals. These electrical signals are received by the sound processor 436, which is configured to execute sound processing and coding to convert the electrical signals into processed signals that represent the detected sound signals. The processed signals are then provided to the output transducer 424 via a lead 477. The output transducer 424 is configured to utilize the processed signals to mechanically stimulate the recipient. That is, the output transducer 424 is mechanically coupled to the stapes 114 via a coupling element 446. As such, the coupling element 446 relays vibration generated by the output transducer 424 to the stapes 114 which, in turn, causes oval window 110 to vibrate. Such vibration of the oval window 110 sets up waves of fluid motion within the cochlea 116 which, in turn, activates hair cells (not shown) that line the inside of the cochlea 116. Activation of these hair cells causes appropriate nerve impulses to be transferred through the spiral ganglion cells and the auditory nerve 118 to the brain (not shown), where they are perceived as sound. As noted above, in the embodiment of FIGS. 1A and 1B, the stapes 114 is disarticulated from the malleus 112 and the incus 113. As such, the vibration of the malleus 112 and/or the incus 113 in response to the impingement of the sound signal 107 on the tympanic membrane 104 does not cause vibration of the stapes 114. Similarly, vibration delivered to the stapes 114 by the output transducer 424 does not cause vibration of the malleus 112 or the incus 113.

As detailed above, the totally implantable acoustic implant 400 is a totally implantable device that is configured to: (1) detect/receive sound signals from within the recipient, (2) process the sound signals, and (3) use the sound signals to generate stimulation (i.e. mechanical vibration) for delivery to the recipient to evoke perception of the sound signals. Also as noted above, the sound signals are detected via one or more implantable sound sensors (e.g., implantable microphone 440). As described above with reference to FIGS. 1A and 1B, it may not always be desirable to enable all recipients to make use of an implantable sound sensor. As such, in accordance with embodiments presented herein, the totally implantable acoustic implant 400 can be configured to: (1) operate with an external device that is configured to detect sound signals (i.e., an external sound source), and (2) to restrict/limit the use of sound signals detected by any implantable sound sensor 440 in stimulating the recipient. More specifically, in accordance with embodiments presented herein, the external sound source provides sound signals to the totally implantable acoustic implant 400 and the totally implantable acoustic implant 400 is configured to use those signals from the external sound source to stimulate the recipient. However, when the external device is not present/available to provide sound signals to the recipient, the totally implantable acoustic implant 400 restricts/limits the use of sound signals detected at the implantable sound sensor 440.

For example, totally implantable acoustic implant 400 is configured to operate with at least one external sound source 452. The totally implantable acoustic implant 400 and the external sound source 452 are sometimes collectively referred to herein as an acoustic implant system 455. For ease of illustration, FIGS. 4A and 4B illustrate the external sound source 452 in the form of a behind-the-ear (BTE) sound processing unit. However, it is to be appreciated that totally implantable cochlear implants in accordance with embodiments presented herein may be used with any of a variety of devices that are configured to provide sound signals, including BTE units, off-the-ear headpiece units (i.e., button processor units), in-the-ear (ITE) devices, wireless microphones, etc.

The BTE sound processing unit 452 in FIGS. 4A and 4B includes a housing 456 that is configured to be worn on the outer ear 105 of the recipient. The BTE sound processing unit 452 also comprises one or more external sources which, in the examples of FIGS. 4A and 4B, comprise an external microphone 454 and an auxiliary input (e.g., telecoil, audio input port, etc.) 457. Although FIG. 4B illustrates the external microphone within housing 456, it is to be appreciated that the external microphone 454 may also or alternatively be located outside of the housing.

The BTE sound processing unit 452 further comprises a sound processor 458, a power source 460 (e.g., a battery), and a wireless communications interface 462. The external sound sources (e.g., external microphone 454 and/or the auxiliary input 457) are configured to detect/receive sound signals. In this example, the sound processor 458 is configured to process electrical signals generated by the external sound sensors and to generate processed sound signals therefrom. The wireless communications interface 462 is configured to send the processed sound signals generated by the sound processor 458 to the wireless communications interface 439 totally implantable acoustic implant 400. That is, the wireless communications interface 462 comprises one or more elements that enable the BTE sound processing unit 452 to wirelessly communicate with the totally implantable acoustic implant 400.

When the BTE sound processing unit 452 is able to provide external sound signals to the totally implantable acoustic implant 400, the totally implantable acoustic implant is configured so as to operate (by default) in an "external hearing mode." In the external hearing mode, the totally implantable acoustic implant 400 uses the sound signals received from the BTE sound processing unit 452 to stimulate the recipient. It is to be appreciated that the totally implantable acoustic implant 400 could operate in a number of different manners so as to use external sound signals to stimulate the recipient (e.g., suppress any internal sound signals, mix the internal sounds with the sound signals received from the BTE sound processing unit 452, etc.).

In accordance with embodiments presented herein, the totally implantable acoustic implant 400 is configured to operate in a "restricted hearing mode" when the totally implantable acoustic implant 400 is not in communication with BTE sound processing unit 452 (or another external sound source) and/or the BTE sound processing unit 452 is otherwise unable to provide external sound signals to the cochlear implant. That is, when the totally implantable acoustic implant 400 determines that the BTE sound processing unit 452 is unable to provide external sound signals, the implant controller 450 is configured restrict/limit operations of the totally implantable acoustic implant 400.

The restricted hearing mode of totally implantable acoustic implant 400 may take a number of different forms that can be selected based on a number of different factors. In general, the restricted hearing mode may be similar to that described above in FIGS. 1A and 1B with reference to cochlear implant 100. For example, in certain embodiments, when the totally implantable acoustic implant 400 enters the restricted hearing mode, the implant controller 450 is configured to substantially immediately limit (e.g., disable/prevent, dampen, etc.) the delivery of stimulation to the recipient, irrespective of the charge level in the implantable battery 434. That is, in these embodiments the implant controller 450 configures one or more of the sound processor 436 or the output transducer (stimulator unit) 424 so as to limit the generation of stimulation signals based on any internal sound signals detected at the implantable microphone 440. In one alternative embodiment, when the totally implantable acoustic implant 400 enters the restricted hearing mode, the implant controller 450 is configured to substantially immediately limit operation of the totally implantable acoustic implant (e.g., power down the totally implantable acoustic implant). In each of these embodiments, the implant controller 450 could initiate the generation of at least one of an external audible or visual alert to a caretaker or other user indicating that the totally implantable acoustic implant 400 is no longer delivering stimulation signals to the recipient.

As described above with reference to FIGS. 1A and 1B, the restricted hearing mode of an implantable auditory prosthesis in accordance with embodiments presented herein, such as totally implantable acoustic implant 400, is configured to generally limit the use of internal sound signals for generation of stimulation for delivery to the recipient. However, further embodiments may enable additional operations when, for example, the totally implantable acoustic implant 400 first enters the restricted mode, periodically while in the restricted hearing mode, etc. These additional operations may be similar to those described above with reference to FIGS. 1A and 1B. For example, the implant controller 450 may be configured to enable the totally implantable acoustic implant 400 to stimulate the recipient using internal sound signals for only a selected/limited period of time, selectively enable the delivery of stimulation to the recipient based on one or more attributes of the internal sound signals (e.g., a level/loudness of the sound signals, a sound/acoustic environment in which the recipient is located, a noise level, etc.), selectively enable the delivery of stimulation to the recipient during certain time periods each day, etc. Any of the above or other embodiments of the restricted hearing mode may be implemented alone, in various combinations, or may include other extensions/restrictions. In addition, the implant controller 452 may be generally configured to cause the totally implantable acoustic implant 400 to initiate the generation of at least one of an audible or visual alert when the controller has performed various actions.

It is to be appreciated that the specific operations that are enabled in the restricted hearing mode of totally implantable acoustic implant 400 may depend on a number of different factors and may be different for individual recipients. As such, the operations of the implant controller 450 and other components of the totally implantable acoustic implant 400 during the restricted hearing mode, as well as when the totally implantable acoustic implant 400 enters the restricted hearing mode, can be set/programmed by a clinician/audiologist based on the needs of a user. That is, the restricted hearing mode of an implantable auditory prosthesis, such as totally implantable acoustic implant 400, can be configured/programmed by a clinician during, for example, a fitting session, as described above.

When compared with external sound sensors (i.e., sensors that are outside the recipient's body), implantable sound sensors can provide a lower signal quality. This lower signal quality may be a result of a number of different factors, such as sound attenuation/damping caused by the recipient's skin/tissue, increased noise levels (e.g., body noises), sensor location and/or orientation (e.g. below and/or behind the auricle of the recipient) etc., that can be avoided with external sound sensors. Nonetheless, implantable sound sensors provide acceptable signal quality for many recipients, particularly recipients with developed language skills, recipients with previous experience, etc. As such, the use of implantable sound sensors provide recipient's with the ability to have a truly "invisible" prostheses (i.e., since there are no external components, the prosthesis is invisible to others).

Although many users are not significantly affected by the lower signal quality of implantable sound sensor(s), this lower signal quality could be problematic for certain recipients, such as pediatric recipients, child recipients, etc. For example, the lower signal quality of the implantable sound sensor(s) could negatively impact the development of speech/language skills in pediatric or child recipients. As a result, the use of implantable sound sensors for these types of recipients may in some circumstances be undesirable and, potentially, unacceptable since such use could harm the recipient from a speech development perspective. As such, the use of implantable sound sensors could operate as a deterrent to the implantation of totally implant cochlear implants in certain recipients.

Once implanted, cochlear implants and other prostheses may not necessarily be easily explantable/removable for upgrade. As such, many auditory prostheses are generally viewed as a semi-permanent or at least a long-term commitment on the part of a recipient. Due, at least in part to the long-term commitment, there is a general desire to implant a recipient with the newest technologies that, accordingly, provide the recipient with maximum flexibility and benefit. Therefore, although the use of implantable sound sensors may be undesirable for certain recipients, this factor must be weighed against the long-term commitment and the desire to implant a recipient with, for example, a totally implantable auditory prosthesis (e.g., cochlear implant, acoustic implant, etc.).

As described in detail above, presented herein are techniques that allow a majority of recipients to receive a totally implantable cochlear implant, a totally implantable acoustic implant, etc., while simultaneously addressing the concern that the use of implantable sound sensors could negatively impact the recipient. More specifically, an implantable auditory prosthesis (e.g., totally implantable cochlear implant, a totally implantable acoustic implant, etc.) in accordance with embodiments presented herein includes at least one implantable sound sensor that is configured to detect sound signals from within a recipient and to use these internally detected sound signals for use in stimulating the recipient. However, the implantable auditory prosthesis can also be configured to receive sound signals from an external sound source and to use the externally detected sound signals for use in stimulating the recipient. The techniques presented herein configure the implantable auditory prosthesis to use the sound signals received from the external sound source to stimulate the recipient, while restricting the use of sound signals detected at the implantable sound sensor when the external sound source is not present/available to provide sound signals to the implantable auditory prosthesis.

The techniques presented herein enable a clinician to selectively limit, restrict, or otherwise control the use of invisible hearing for certain recipients of an implantable hearing prosthesis that includes an implantable sound sensor, sound processor, etc. The objective is to encourage use of external sound signals while the recipient's understanding of language is developing as the sound quality (using an external microphone) is perceived to be better. The techniques presented can, accordingly, provide assurance that a child or pediatric recipient is provided with optimum sound quality while they are still developing language skills and provide comfort to the guardian/caregiver that the child is given the best opportunity to hear. The techniques presented herein may also extend the cycle life of an implanted battery by limiting the discharge voltage.

It is to be appreciated that the embodiments presented herein are not mutually exclusive and may be combined in various manners.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A totally implantable component of a hearing prosthesis system, wherein the totally implantable component comprises:
   an implantable microphone;
   an implantable battery;
   a stimulator unit configured to stimulate a recipient of the totally implantable component to evoke a hearing percept when the totally implantable component is in communication with an external component of the hearing prosthesis system; and
   a controller configured to determine that the totally implantable component is not in communication with the external component and, in response, initiate a secondary mode to limit stimulation of the recipient, irrespective of the charge level in the implantable battery, when the totally implantable component is not in communication with the external component,
   wherein the totally implantable component remains operational in the secondary mode.

2. The totally implantable component of claim 1, wherein to limit stimulation of the recipient when the totally implantable component is not in communication with the external component, the controller is configured to:
   enable stimulation of the recipient for only a limited period of time after determining that the totally implantable component is not in communication with the external component.

3. The totally implantable component of claim 1, wherein to limit stimulation of the recipient when the totally implantable component is not in communication with the external component, the controller is configured to:
   analyze one or more attributes of sound signals detected at the implantable microphone and to selectively enable stimulation of the recipient using the sound signals only when the one or more attributes of the sound signals satisfy predetermined criteria.

4. The totally implantable component of claim 3, wherein the one or more attributes include a sound class of the sound signals.

5. The totally implantable component of claim 3, wherein the one or more attributes include a level of the sound signals.

6. The totally implantable component of claim 1, wherein to limit stimulation of the recipient when the totally implantable component is not in communication with the external component, the controller is configured to:
   determine a current time-of-day, and wherein the controller is configured to selectively enable stimulation of the recipient only during certain times of the day.

7. The totally implantable component of claim 1, wherein the controller is configured to cause the implantable auditory prosthesis to initiate the generation of at least one of an audible or visual alert when the controller limits stimulation of the recipient.

8. The implantable component of claim 1, wherein the implantable component is selected from the group comprising a totally implantable cochlear implant and a totally implantable acoustic implant.

9. An implantable auditory prosthesis implantable in a recipient, comprising:
   at least one implantable sound sensor configured to detect internal sound signals from within the recipient;
   a stimulator unit operable to generate stimulation signals for delivery to a recipient of the auditory prosthesis; and
   a controller configured to determine that the implantable auditory prosthesis is unable to communicate with at least one external sound source and, in response, initiate a secondary mode to restrict usage of the internal sound signals in the generation of stimulation signals for delivery to the recipient when the implantable auditory prosthesis is unable to communicate with at least one external sound source, wherein the totally implantable component remains operational in the secondary mode.

10. The implantable auditory prosthesis of claim 9, wherein the implantable auditory prosthesis comprises an implantable coil configured to be inductively coupled to an external coil of the at least one external sound source, and wherein the controller determines that the implantable auditory prosthesis is unable to communicate with at least one external sound source when the implantable coil is inductively decoupled from the external coil.

11. The implantable auditory prosthesis of claim 9, wherein to restrict usage of the internal sound signals in the generation of stimulation signals for delivery to the recipient, the controller is configured to limit the stimulator unit from generating stimulation signals based on the internal sound signals.

12. The implantable auditory prosthesis of claim 11, wherein to restrict usage of the internal sound signals in the generation of stimulation signals for delivery to the recipient, the controller is configured to:
   enable the stimulator unit to use the internal sound signals in the generation of stimulation signals for only a limited period of time after determining that the implantable auditory prosthesis is unable to communicate with at least one external sound source.

13. The implantable auditory prosthesis of claim 11, wherein to restrict usage of the internal sound signals in the generation of stimulation signals for delivery to the recipient, the controller is configured to:
   analyze one or more attributes of the sound signals and, when the implantable auditory prosthesis is unable to communicate with at least one external sound source, to selectively enable the stimulator unit to use the internal sound signals in the generation of stimulation signals only when the one or more attributes of the sound signals satisfy predetermined criteria.

14. The implantable auditory prosthesis of claim 13, wherein the one or more attributes include at least one of a sound class of the internal sound signals or a loudness of the internal sound signals.

15. The implantable auditory prosthesis of claim 9, wherein to restrict usage of the internal sound signals in the generation of stimulation signals for delivery to the recipient, the controller is configured to:
   determine a current time-of-day, and wherein the controller is configured to selectively enable usage of the internal sound signals in the generation of stimulation signals for delivery to the recipient only during certain times of the day.

16. The implantable auditory prosthesis of claim 9, wherein the controller is configured to cause the implantable auditory prosthesis to initiate the generation of at least one of an audible or visual alert when the controller restrict usage of the internal sound signals.

17. A fitting system, comprising:
   a device interface for communication with an implantable auditory prosthesis implanted in a recipient, wherein the implantable auditory prosthesis comprises an implantable microphone and a stimulator unit;
   a user interface configured to receive an input from a user restricting operation of the implantable auditory prosthesis in a secondary mode in which the implantable auditory prosthesis is not in communication with any external sound sources, but remains at least partially operational in the secondary mode; and one or more processors configured to process the input to generate one or more instructions, where the instructions represent the one or more restrictions on the operation of the implantable auditory prosthesis when the implantable auditory prosthesis detects that the implantable auditory prosthesis is not in communication with any external sound sources, and to send the one or more instructions to the implantable auditory prosthesis for instantiation thereof.

18. The fitting system of claim 17, wherein the one or more processors are configured to generate instructions representing limitations on the ability of the implantable auditory prosthesis to, when in the secondary mode, use sound signals received by the implantable microphone for stimulating the recipient when the implantable auditory prosthesis is not in communication with any external sound sources.

19. The fitting system of claim 18, wherein the one or more processors are configured to generate instructions indicating that stimulation of the recipient using sound signals received by the implantable microphone is to be enabled for only a limited period of time after determining that the implantable auditory prosthesis is not in communication with any external sound sources then subsequently disabled thereafter.

20. The fitting system of claim 18, wherein the one or more processors are configured to generate instructions indicating that stimulation of the recipient using sound signals received by the implantable microphone is to be enabled only when one or more attributes of the sound signals satisfy predetermined criteria.

* * * * *